US007872756B2

(12) United States Patent
Oda

(10) Patent No.: US 7,872,756 B2
(45) Date of Patent: Jan. 18, 2011

(54) GAS MEASURING APPARATUS AND GAS MEASURING METHOD

(75) Inventor: Naoki Oda, Tokyo (JP)

(73) Assignee: NEC Corporation, Tokyo (JP)

( * ) Notice: Subject to any disclaimer, the term of this patent is extended or adjusted under 35 U.S.C. 154(b) by 189 days.

(21) Appl. No.: 12/356,016

(22) Filed: Jan. 19, 2009

(65) Prior Publication Data

US 2010/0018289 A1 Jan. 28, 2010

(30) Foreign Application Priority Data

Jan. 24, 2008 (JP) .............................. 2008-013617

(51) Int. Cl.
*G01N 21/00* (2006.01)
*G01B 9/02* (2006.01)
*G01J 5/02* (2006.01)
(52) U.S. Cl. ................ 356/456; 250/339.13; 250/338.5
(58) Field of Classification Search ............ 250/339.02, 250/339.08, 339.09, 339.13, 338.1, 338.5; 356/451, 452, 456
See application file for complete search history.

(56) References Cited

U.S. PATENT DOCUMENTS

| 6,531,701 | B2 * | 3/2003 | Chou et al. ............ 250/339.08 |
| 7,495,218 | B2 * | 2/2009 | Gopalsami et al. ....... 250/336.1 |
| 7,687,776 | B2 * | 3/2010 | Baliga et al. ............. 250/338.5 |

OTHER PUBLICATIONS

R. Harig and G. Matz, "Toxic Cloud Imaging by Infrared Spectrometry: A Scanning FTIR System for Identification and Visualization", Field Analytical Chemistry and Technology, vol. 5 (1-2), and pp. 75-90, 2001.

* cited by examiner

*Primary Examiner*—Hwa S. A Lee

(57) ABSTRACT

A gas measuring apparatus includes: an infrared detecting section that receives an infrared ray from a measurement area and outputs infrared spectrum data relating to the infrared ray; a variation detecting section that detects, by using the infrared spectrum data, a variation in intensity of the infrared ray, which is caused in the infrared ray that radiates from the measurement area and which is caused by a measuring object gas in the measurement area; a converting section that converts the infrared spectrum data to radiance temperature spectrum data which represent wavelengths in an infrared region and radiance temperatures at each wavelength; a background temperature detecting section that detects, as background temperature of the measuring object gas, a maximum radiance temperature from among radiance temperatures represented by the radiance temperature spectrum data; a gas temperature detecting section that detects the temperature of the measuring object gas by using a radiance temperature in a wavelength band included in the water vapor absorption band in the infrared region from among the radiance temperatures represented by the radiance temperature spectrum data; and a computing section that computes surface density of the measuring object gas on the basis of the variation in intensity of the infrared ray, the background temperature of the measuring object gas, and the temperature of the measuring object gas.

15 Claims, 13 Drawing Sheets

Fig. 11

| DISTANCE(m) | WAVELENGTH RANGE REPRESENTING GAS HUMIDITY (TEMPERATURE ACCURACY 0.2°C) | WAVELENGTH RANGE REPRESENTING BACKGROUND TEMPERATURE (TEMPERATURE ACCURACY 0.2°C) |
|---|---|---|
| 50 | 7–7.3 μm | 8.9–10.4, 10.7–11 μm |
| 100 | 7–7.3 μm | 8.9–10.4, 10.7–11 μm |
| 200 | 7–7.6 μm | 9.5–10.4, 10.7–10.9 μm |
| 500 | 7–7.6 μm | 10.0–10.4, 10.7 μm |
| 1000 | 7–7.9 μm | 10.0–10.1, 10.4, 10.7 μm |

GAS DISTRIBUTION IS SUPERIMPOSED ON INFRARED IMAGE OF WAVELENGTH OF 7 TO 14 MICROMETERS. COLORED SECTION: DISTRIBUTION OF $SF_6$ GAS (USING ABSORPTION LINE OF 10.5 MICROMETERS)

GAS MEASURING APPARATUS AND GAS MEASURING METHOD

This application is based upon and claims the benefit of priority from Japanese patent application No. 2008-013617, filed on Jan. 24, 2008, the disclosure of which is incorporated herein in its entirety by reference.

BACKGROUND OF THE INVENTION

1. Field of the Invention

The present invention relates to a gas measuring apparatus and a gas measuring method.

2. Description of the Related Art

In non-patent document 1 (R. Harig and G. Matz, Field Analytical Chemistry and Technology, Vol. 5 (1-2), and pp. 75-90, 2001), there is described a technique in which a processing section identifies a measuring object gas by using a remote gas spectroscopic imaging detector (hereinafter simply referred to as "detector") having a scanning mirror, an optical system, a Fourier spectrometer, and a single element infrared sensor, and measures the spatial distribution and density of the measuring object gas.

For example, in non-patent document 1, there is described a technique in which the temperature of the measuring object gas and the background temperature of the measuring object gas (hereinafter simply referred to as "background temperature") are detected on the basis of the output of the detector, and in which the measuring object gas is identified by using the temperature of the measuring object gas and the background temperature.

The temperature of the measuring object gas and the background temperature are detected as follows.

The processing section first generates infrared spectrum data from the output of the single element infrared sensor. Then, the processing section converts the infrared spectrum data to radiance temperature spectrum data.

The processing section uses, as the background temperature, the maximum radiance temperature in the radiance temperature spectrum data.

The radiance temperature maximum value in the radiance temperature spectrum data corresponds to data of a substance having the highest transmittance (substance which almost transmits light from the background) among substances which exist between the detector and the background of the measuring object gas, that is, corresponds to data of light from the background. For this reason, it is thought that the radiance temperature maximum value most faithfully represents the background temperature among the radiance temperature spectrum data.

Then, the processing section uses, as the temperature of the measuring object gas, the minimum radiance temperature in the wavelength band near the wavelength of 14.5 micrometers in the radiance temperature spectrum data.

The wavelength band near the wavelength of 14.5 micrometer corresponds to the strong absorption band of $CO_2$ (carbon dioxide). For this reason, a part of the light from the background of the measuring object gas having a wavelength near 14.5 micrometers is absorbed by $CO_2$. Therefore, the radiance temperature near the wavelength of 14.5 micrometers in the radiance temperature spectrum data does not depend on the light from the background of the measuring object gas but depends on the amount of absorption by $CO_2$. Further, in the case where the amount of absorption by $CO_2$ is very large, the radiance temperature near the wavelength of 14.5 micrometers in the radiance temperature spectrum data represents the temperature of $CO_2$ gas itself.

Therefore, it is thought that the minimum radiance temperature near the wavelength of 14.5 micrometers in the radiance temperature spectrum data represents the temperature of $CO_2$. At present, $CO_2$ universally exists in the earth's atmosphere. Therefore, it is thought that the temperature of $CO_2$ represents the temperature of the earth's atmosphere. The measuring object gas also exists in the earth's atmosphere. For this reason, it is considered that the temperature of the measuring object gas becomes equal to the temperature of the earth's atmosphere, that is, the temperature of $CO_2$.

The processing section described in non-patent document 1 measures the temperature of the object gas by using $CO_2$ which has a strong absorption band near the wavelength of 14.5 micrometers.

For this reason, the technique described in non-patent document 1 has a restriction in which it is necessary to use, as the infrared sensor, an infrared sensor which is capable of detecting an infrared ray having a wavelength at least up to 14.5 micrometer.

Therefore, in the technique described in non-patent document 1, the usable infrared sensor is restricted, and thereby it is not possible to use, for example, a two-dimensional infrared detector having a cutoff wavelength of 11 micrometer.

SUMMARY OF THE INVENTION

An exemplary object of the present invention is to provide a gas measuring apparatus and a gas measuring method which are capable of solving the above described problem.

A gas measuring apparatus according to an exemplary aspect of the invention includes: an infrared detecting section that receives an infrared ray from a measurement area and outputs infrared spectrum data relating to the infrared ray; a variation detecting section that detects, by using the infrared spectrum data, a variation in intensity of the infrared ray, which is caused in the infrared ray that radiates from the measurement area and which is caused by a measuring object gas in the measurement area; a converting section that converts the infrared spectrum data to radiance temperature spectrum data which represent wavelengths in an infrared region and radiance temperatures at each wavelength; a background temperature detecting section that detects, as background temperature of the measuring object gas, a maximum radiance temperature from among radiance temperatures represented by the radiance temperature spectrum data; a gas temperature detecting section that detects the temperature of the measuring object gas by using a radiance temperature in a wavelength band included in a water vapor absorption band in the infrared region from among the radiance temperatures represented by the radiance temperature spectrum data; and a computing section that computes the surface density of the measuring object gas on the basis of the variation in intensity of the infrared ray, the background temperature of the measuring object gas, and the temperature of the measuring object gas.

A gas measuring method according to an exemplary aspect of the invention, which is performed by a gas measuring apparatus, includes: outputting infrared spectrum data relating to an infrared ray by receiving the infrared ray from a measurement area; detecting, by using the infrared spectrum data, a variation in intensity of the infrared ray, which is caused in the infrared ray that radiates from the measurement area and which is caused by a measuring object gas in the measurement area; converting the infrared spectrum data to radiance temperature spectrum data which represent wavelengths in an infrared region and radiance temperatures at each wavelength; detecting, as background temperature of the measuring object gas, a maximum radiance temperature from among radiance temperatures represented by the radiance temperature spectrum data; detecting the temperature of the measuring object gas by using a radiance temperature in a wavelength band included in a water vapor absorption band in the infrared region from among the radiance temperatures represented by the radiance temperature spectrum data; and computing the surface density of the measuring object gas on the basis of the variation in intensity of the infrared ray, the background temperature of the measuring object gas, and the temperature of the measuring object gas.

The above and other objects, features, and advantages of the present invention will become apparent from the following description with reference to the accompanying drawings which illustrate an example of the present invention.

BRIEF DESCRIPTION OF THE DRAWINGS

FIG. 11 is an illustration showing wavelength ranges used for obtaining temperature (B) of measuring object gas 5a and temperature (A) of background 5c with a temperature accuracy of 0.2° C. from the radiance temperature spectrum data shown in each of FIG. 6 to FIG. 10;

DESCRIPTION OF THE EXEMPLARY EMBODIMENT(S)

In the following, exemplary embodiments according to the present invention will be described with reference to the accompanying drawings.

Figure 1:
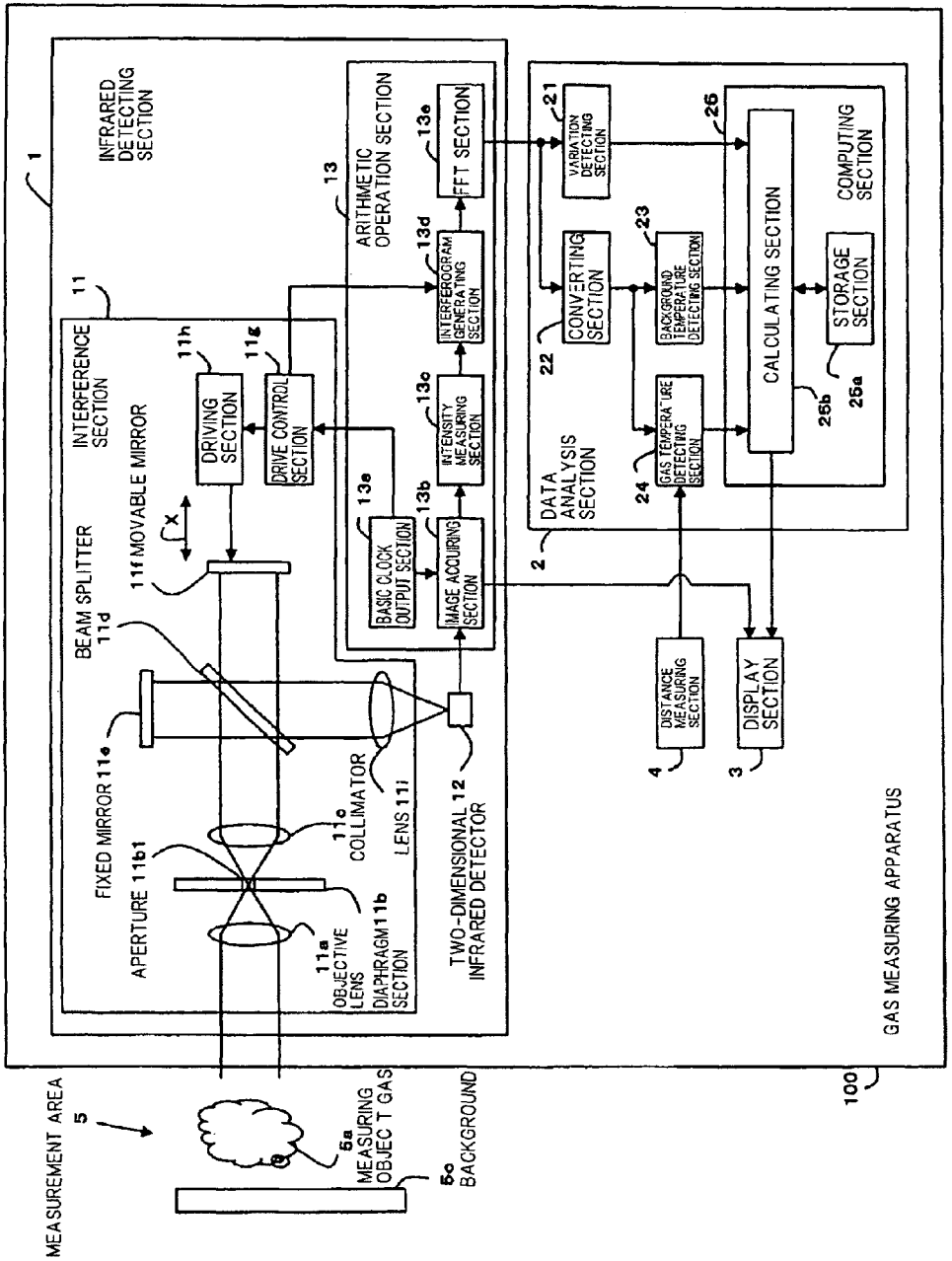
FIG. 1 is a figure showing gas measuring apparatus 100 according to a first exemplary embodiment.

FIG. 1 is a figure showing gas measuring apparatus 100 according to a first exemplary embodiment.

In FIG. 1, gas measuring apparatus 100 includes infrared detecting section 1, data analysis section 2, display section 3, and distance measuring section 4.

Infrared detecting section 1 includes interference section 11, two-dimensional infrared detector 12, and arithmetic operation section 13.

Data analysis section 2 includes variation detecting section 21, converting section 22, background temperature detecting section 23, gas temperature detecting section 24, and computing section 25. Computing section 25 includes storage section 25a, such as a memory, and calculating section 25b.

Interference section 11 includes objective lens 11a, diaphragm section 11b, collimator 11c, beam splitter 11d, fixed mirror 11e, movable mirror 11f, drive control section 11g, driving section 11h, and lens 11i.

Arithmetic operation section 13 includes basic clock output section 13a, image acquiring section 13b, intensity measuring section 13c, and interferogram generating section 13d and FFT section 13e.

Infrared detecting section 1 can be generally referred to as infrared detecting means. Note that infrared detecting section 1 is a Fourier transform infrared spectrometer imaging apparatus in which two-dimensional infrared detector 12 is used as an infrared sensor. The Fourier transform infrared spectrometer imaging apparatus is a related art.

Infrared detecting section 1 receives an infrared ray from measurement area 5, and outputs infrared spectrum data relating to the infrared ray.

Interference section 11 can be generally referred to as interference means.

Interference section 11 divides the infrared ray from measurement area 5 into a plurality of infrared rays, and generates interference light by synthesizing the plurality of infrared rays while changing the optical path difference between the plurality of infrared rays.

Objective lens 11a receives the image (including the infrared ray) of measurement area 5, and supplies the image to collimator 11c via aperture 11b1 provided in diaphragm section 11b.

Collimator 11c converts the image of measurement area 5 into parallel light beams and supplies the parallel light beams of the image of measurement area 5 to beam splitter 11d.

Beam splitter 11d transmits a part of the parallel light beams of the image of measurement area 5 and reflects the remaining part of the parallel light beams, so as to divide the parallel light beam image of measurement area 5 into two images.

Fixed mirror 11e is not moved, and reflects the image reflected by beam splitter 11d, so as to return the reflected image to beam splitter 11d.

Movable mirror 11f reflects the image transmitted through beam splitter 11d while being moved in the direction of arrow X, so as to return the reflected image to beam splitter 11d.

Fixed mirror 11e is not moved, and movable mirror 11f is moved. For this reason, the optical path difference (hereinafter simply referred to as "optical path difference") between the optical path in which the image transmitted through beam splitter 11d is returned to beam splitter 11d by being reflected by movable mirror 11f, and the optical path in which the image reflected by beam splitter 11d is returned to beam splitter 11d by being reflected by fixed mirror 11e, is changed according to the movement of movable mirror 11f.

The image which is returned to beam splitter 11d by being reflected by movable mirror 11f, and the image which is returned to beam splitter 11d by being reflected by fixed mirror 11e, are synthesized by beam splitter 11d so as to be formed into an interference light beam.

Lens 11i supplies the interference light beam to two-dimensional infrared detector 12.

Note that in the case where the optical path, in which the image transmitted through beam splitter 11d is returned to beam splitter 11d by being reflected by movable mirror 11f, is equal to the optical path in which the image reflected by beam splitter 11d is returned to beam splitter 11d by being reflected by fixed mirror 11e, the interference light beam becomes the image of measurement area 5. For this reason, two-dimensional infrared detector 12 also receives the image of measurement area 5.

Drive control section 11g drives driving section 11h at a timing corresponding to a basic clock from basic clock output section 13a, so as to move movable mirror 11f in both directions of arrow X.

Further, drive control section 11g supplies information representing the position of movable mirror 11f, that is, information representing the optical path difference, to interferogram generating section 13d.

Two-dimensional infrared detector 12 can be generally referred to as two-dimensional infrared detecting means. Two-dimensional infrared detector 12 receives the interference light beam.

Arithmetic operation section 13 can be generally referred to as arithmetic operation means.

Arithmetic operation section 13 measures the intensity of the interference light beam on the basis of the output of two-dimensional infrared detector 12. Arithmetic operation section 13 generates an interferogram which represents the relationship between the intensity of the interference light beam and the optical path difference. Arithmetic operation section 13 generates infrared spectrum data of the infrared ray from measurement area 5 by Fourier transforming the interferogram, and outputs the infrared spectrum data.

Basic clock output section 13a outputs a basic clock.

Image acquiring section 13b acquires the output of two-dimensional infrared detector 12 at a timing corresponding to the basic clock. Image acquiring section 13b supplies the output of two-dimensional infrared detector 12 to both display section 3 and intensity measuring section 13c.

Intensity measuring section 13c measures the intensity of the interference light beam on the basis of the output of two-dimensional infrared detector 12. Intensity measuring section 13c supplies the measurement result of the intensity of the interference light beam to interferogram generating section 13d.

Interferogram generating section 13d generates an interferogram, which represents the relationship between the intensity of the interference light beam and the optical path difference, on the basis of the measurement result of the intensity of the interference light beam and which is supplied by intensity measuring section 13c, and on the basis of the information which represents the optical path difference and which is supplied by drive control section 11g. Interferogram generating section 13d supplies the interferogram to FFT section 13e.

FFT section 13e generates infrared spectrum data relating to the infrared ray from measurement area 5 by Fourier transforming the interferogram. FFT section 13e supplies the infrared spectrum data to data analysis section 2, specifically, to variation detecting section 21 and converting section 22.

Data analysis section 2 can be generally referred to as data analysis means. Data analysis section 2 computes the surface density of measuring object gas 5a by using the infrared spectrum data.

Variation detecting section 21 can be generally referred to as variation detecting means.

By using the infrared spectrum data, variation detecting section 21 detects a variation in intensity of the infrared ray which is included in the infrared rays from measurement area 5 and which is varied by measuring object gas 5a in measurement area 5. Variation detecting section 21 supplies the variation in intensity of the infrared ray to computing section 25.

Converting section 22 can be generally referred to as conversion means.

Converting section 22 converts the infrared spectrum data to radiance temperature spectrum data which represent wavelengths in an infrared region and the radiance temperatures at each wavelength. Converting section 22 supplies the radiance temperature spectrum data to both background temperature detecting section 23 and gas temperature detecting section 24.

Background temperature detecting section 23 can be generally referred to as background temperature detecting means.

Background temperature detecting section 23 detects a maximum radiance temperature from among the radiance temperatures represented by the radiance temperature spectrum data as a temperature (background temperature) of background 5c of measuring object gas 5a. Background temperature detecting section 23 supplies the background temperature of measuring object gas 5a to computing section 25.

Gas temperature detecting section 24 can be generally referred to as gas temperature detecting means.

Gas temperature detecting section 24 detects the temperature of measuring object gas 5a by using a radiance temperature in a wavelength band included in the water vapor absorption band in the infrared region from among the radiance temperatures represented by the radiance temperature spectrum data. Gas temperature detecting section 24 supplies the temperature of measuring object gas 5a to computing section 25.

Gas temperature detecting section 24 uses, for example, a wavelength band included in the wavelength band of 5 to 8 micrometers, as the wavelength band included in the water vapor absorption band in the infrared region. Note that the wavelength band of 5 to 8 micrometers is known as the water vapor absorption band in the infrared region.

Computing section 25 can be generally referred to as computing means.

Computing section 25 computes the surface density of measuring object gas 5a on the basis of the variation in intensity of the infrared ray, the background temperature of measuring object gas 5a, and the temperature of measuring object gas 5a. Computing section 25 supplies the surface density of measuring object gas 5a to display section 3.

Storage section 25a can be generally referred to as storage means. Storage section 25a stores various data relating to measuring object gas 5a.

Calculating section 25b can be generally referred to as calculating means. Calculating section 25b calculates the surface density of measuring object gas 5a on the basis of the variation in intensity of the infrared ray, the background temperature of measuring object gas 5a, the temperature of measuring object gas 5a, and the data in storage section 25a.

Display section 3 can be generally referred to as display means.

Display section 3 displays a video image (for example, an image of measurement area 5) corresponding to the output of two-dimensional infrared detector 12, on the basis of the output of two-dimensional infrared detector 12 from image acquiring section 13b.

Further, display section 3 displays the surface density of measuring object gas 5a on the video image corresponding to the output of two-dimensional infrared detector 12.

Distance measuring section 4 can be generally referred to as distance measuring means.

Distance measuring section 4 measures the distance to background 5c of measuring object gas 5a. Distance measuring section 4 supplies the measurement result of the distance to background 5c to gas temperature detecting section 24.

Gas temperature detecting section 24 adjusts, on the basis of the measurement result of the distance to background 5c, the wavelength band which is used to measure the temperature of measuring object gas 5a and which is included in the water vapor absorption band in the infrared region. For example, gas temperature detecting section 24 increases the width of the wavelength band included in the water vapor absorption band in the infrared region, as the increase in the measured distance. Note that gas temperature detecting section 24 may reduce the width of the wavelength band representing the background temperature as the increase in the measured distance.

Note that in the exemplary embodiment, it is assumed that in infrared detecting section 1, a wave number resolution is set to 10 cm$^{-1}$ (corresponding to $\Delta\lambda$=0.1 micrometer in the case of a wavelength of 10 micrometers) and a wave number range is set to 1430 to 833 cm$^{-1}$ (7.0 to 12 um).

Specifically, the maximum value ($X_{OPDMAX}$) of the optical path difference is set to 500 um. In other words, the maximum movable distance ($X_{MechMAX}$) of movable mirror 11f is set to 250 um.

Further, arithmetic operation section 13 samples the output of two-dimensional infrared detector 12 each time the optical path difference is changed by 8.4 um ($\Delta X_{OPD}$=8.4 um). In other words, arithmetic operation section 13 samples the output of two-dimensional infrared detector 12 each time movable mirror 11f is moved by 4.2 um ($\Delta X_{Mech}$=4.2 um).

Further, the number of samplings is set to 60 (in the case of Single-sided interferogram).

Further, movable mirror 11f is driven stepwise for each $\Delta X_{Mech}$=4.2 um by 16 steps in the left direction and by 60 steps in the right direction (for a total of 76 steps). The step drive and the output of two-dimensional infrared detector 12 are performed at every 10 ms (=5 ms+5 ms). In this case, the acquisition time of the interferogram becomes 0.8 sec.

Further, two-dimensional infrared detector 12 is formed of HgCdTe, so as to have a pixel number of 320×240, a pixel pitch of 30 micrometer, a frame rate of 5 to 200 Hz, and an integration time of 3 microsec to 20 msec, and has an NETD (Noise Equivalent Temperature Difference) smaller than 30 mK.

Figure 2:
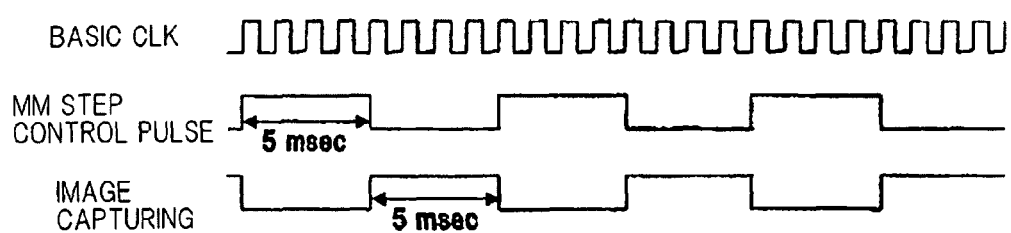
FIG. 2 is a timing chart for explaining a part of an operation of infrared detecting section 1.

FIG. 2 is a timing chart representing examples of the basic clock, the movable mirror step control pulse, and the image pickup timing.

Note that the specification of infrared detecting section 1 is not limited to the above described specification and can be suitably changed.

Next, an operation of the gas measuring apparatus will be described.

Figure 3:
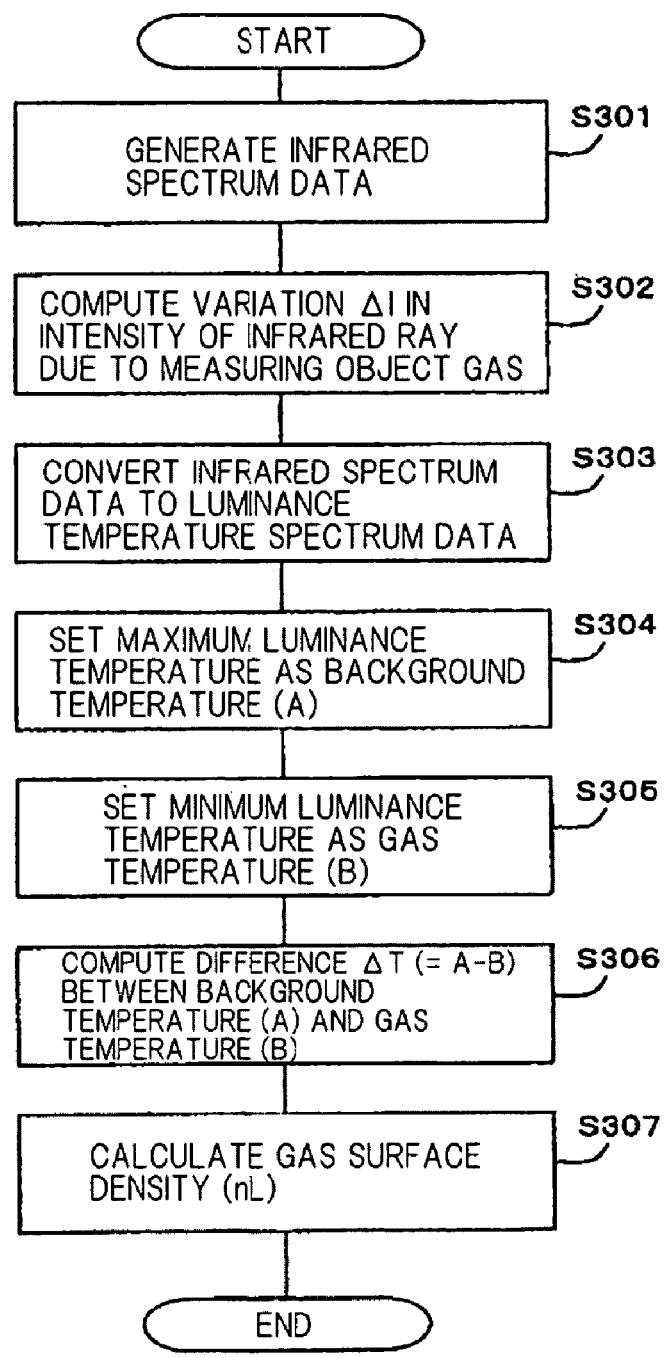
FIG. 3 is a flow chart for explaining an operation of gas measuring apparatus 100.

FIG. 3 is a flow chart for explaining the operation of gas measuring apparatus 100.

Figure 4:
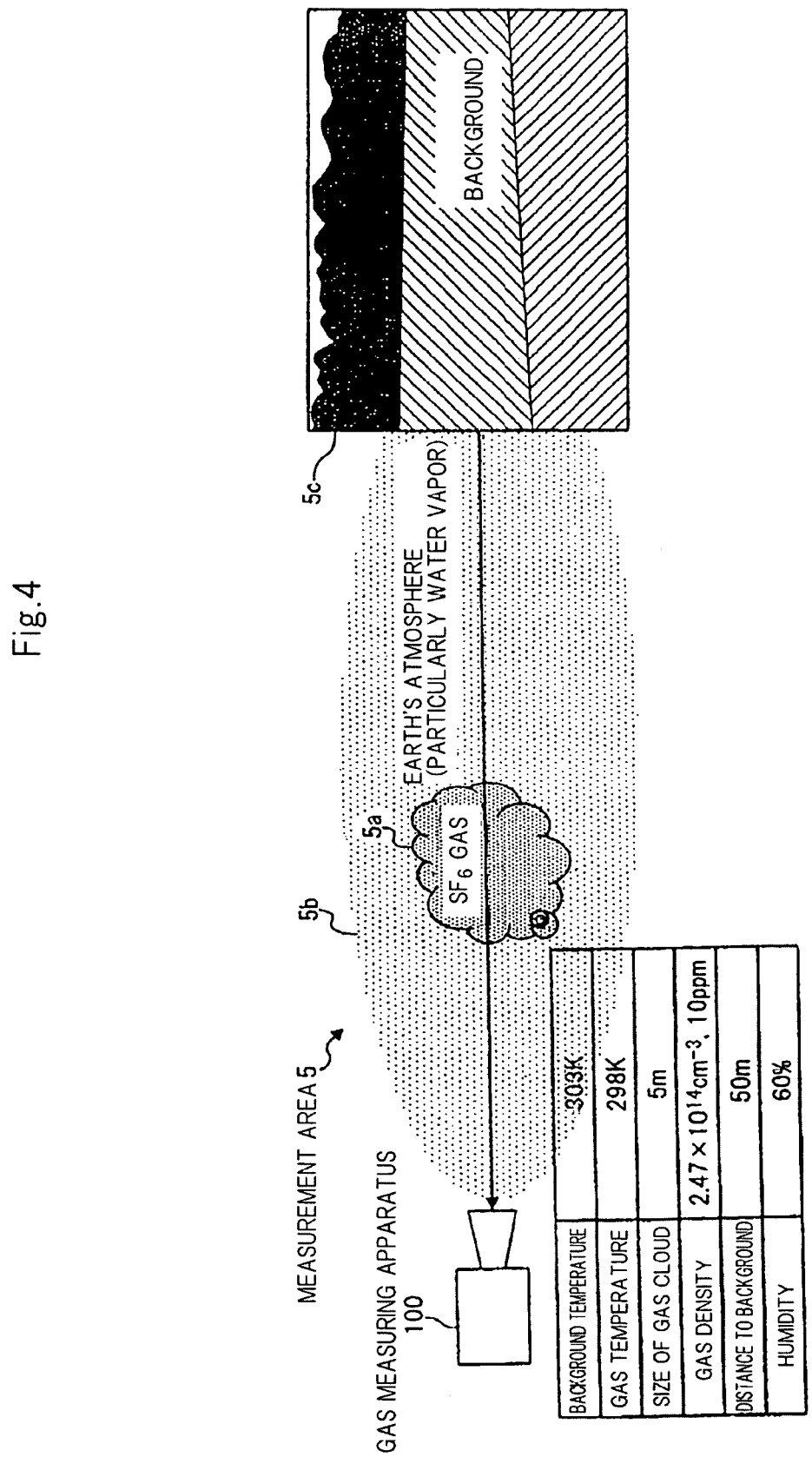
FIG. 4 is an illustration showing a relationship between gas measuring apparatus 100 and measurement area 5 (in which measuring object gas 5a, earth's atmosphere 5b, and background 5c are included)

In the following, there will be described an example in which SF$_6$ is used as measuring object gas 5a as shown in FIG. 4. Note that measuring object gas 5a is not limited to SF$_6$ and can be suitably changed.

FIG. 4 is an illustration showing the relationship between gas measuring apparatus 100 and measurement area 5 (including measuring object gas 5a, earth's atmosphere 5b, and background 5c). In FIG. 4, it is assumed that the temperature of background 5c is 303 K, that the temperature of measuring object gas 5a is 298 K, that the diameter of measuring object gas 5a is 5 m, that the density of measuring object gas 5a is 2.47×10$^{14}$ cm$^{-3}$ or 10 ppm, that the distance to background 5c is 50 m, and that the humidity is 60%.

In step 301, infrared detecting section 1 receives an infrared ray from measurement area 5, and generates infrared spectrum data of the infrared ray. Infrared detecting section 1 supplies the infrared spectrum data to variation detecting section 21 and converting section 22.

Figure 5:
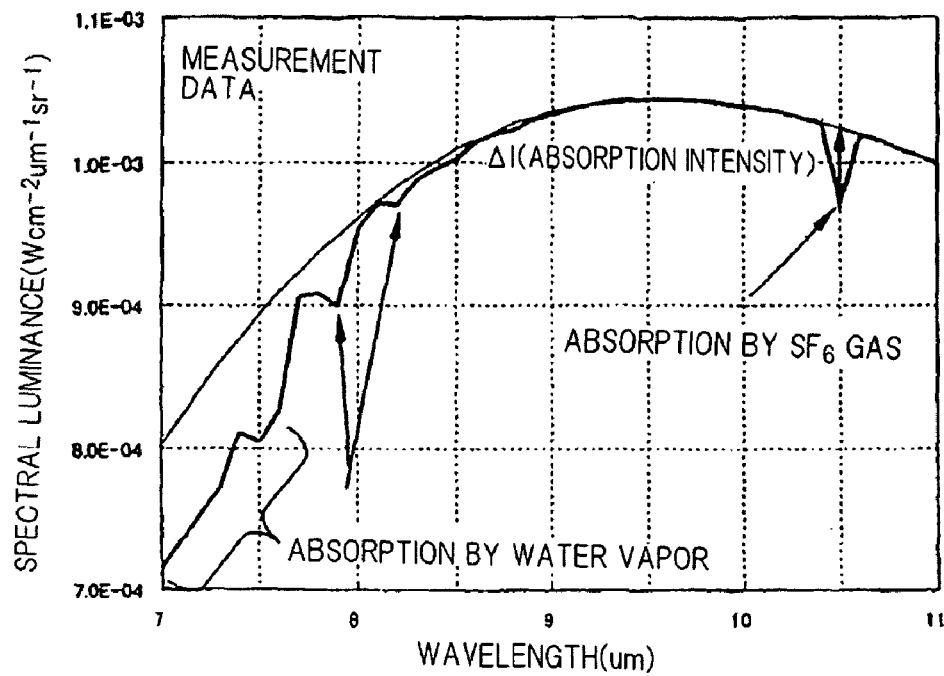
FIG. 5 is an illustration showing infrared spectrum data (measurement data) corresponding to FIG. 4.

FIG. 5 is an illustration showing the infrared spectrum data (measurement data) corresponding to FIG. 4.

Then, in step 302, variation detecting section 21 detects, by using the infrared spectrum data, a variation in intensity of the infrared ray which is included in the infrared rays that radiates from measurement area 5 and which is varied by measuring object gas 5a in measurement area 5.

For example, variation detecting section 21, in which an absorption band of measuring object gas (SF$_6$) 5a is stored beforehand, detects by performing image analysis processing, and the like, the variation ($\Delta I$ shown in FIG. 5) in intensity of the infrared ray in the absorption band of measuring object gas (SF$_6$) 5a, and which is shown in the infrared spectrum data.

Variation detecting section 21 supplies the variation ($\Delta I$) in the infrared intensity to computing section 25.

Further, in step 303, converting section 22 converts the infrared spectrum data to radiance temperature spectrum data which represent wavelengths in the infrared region and the radiance temperatures at each wavelength, by using the known black body radiation formula (Planck's formula) described in non-patent document 1. Converting section 22 supplies the radiance temperature spectrum data to background temperature detecting section 23 and gas temperature detecting section 24.

Figure 6:
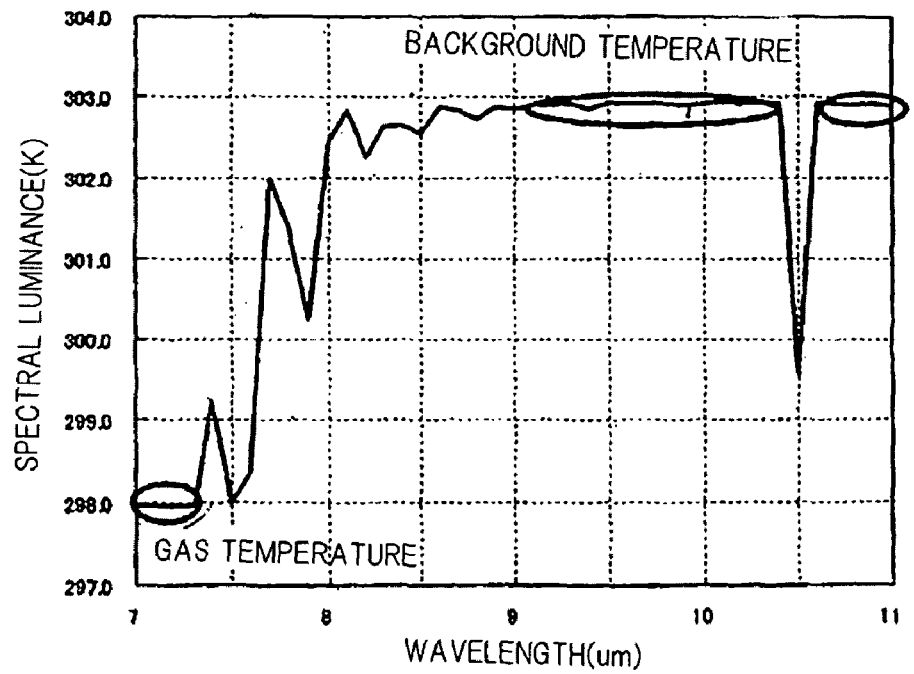
FIG. 6 is an illustration showing radiance temperature spectrum data converted from the infrared spectrum data shown in FIG. 5.
Figure 7:
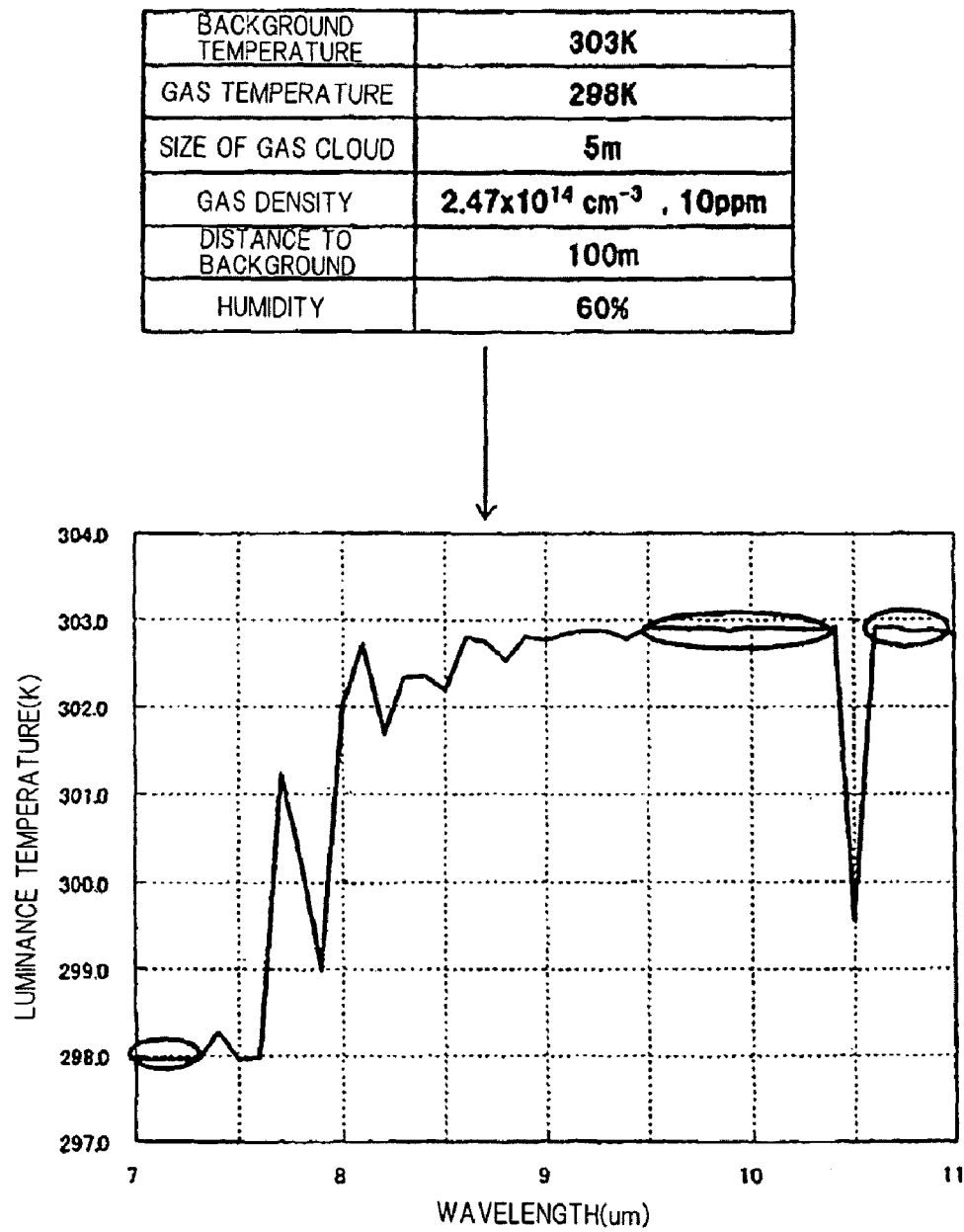
FIG. 7 is an illustration showing radiance temperature spectrum data in the case where the distance to background 5c is changed in FIG. 4.
Figure 8:
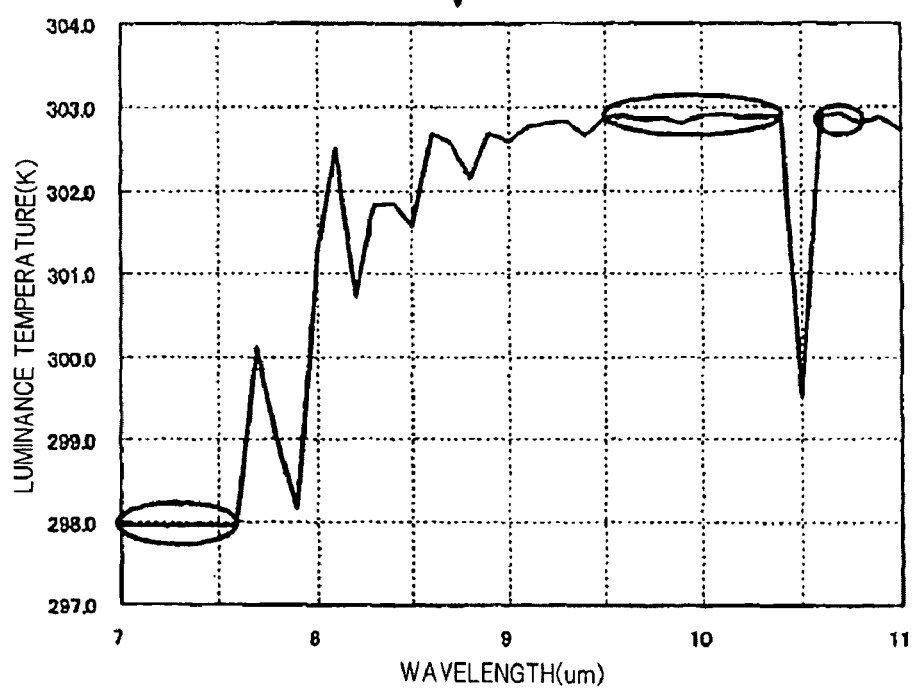
FIG. 8 is an illustration showing radiance temperature spectrum data in the case where the distance to background 5c is changed in FIG. 4.
Figure 9:
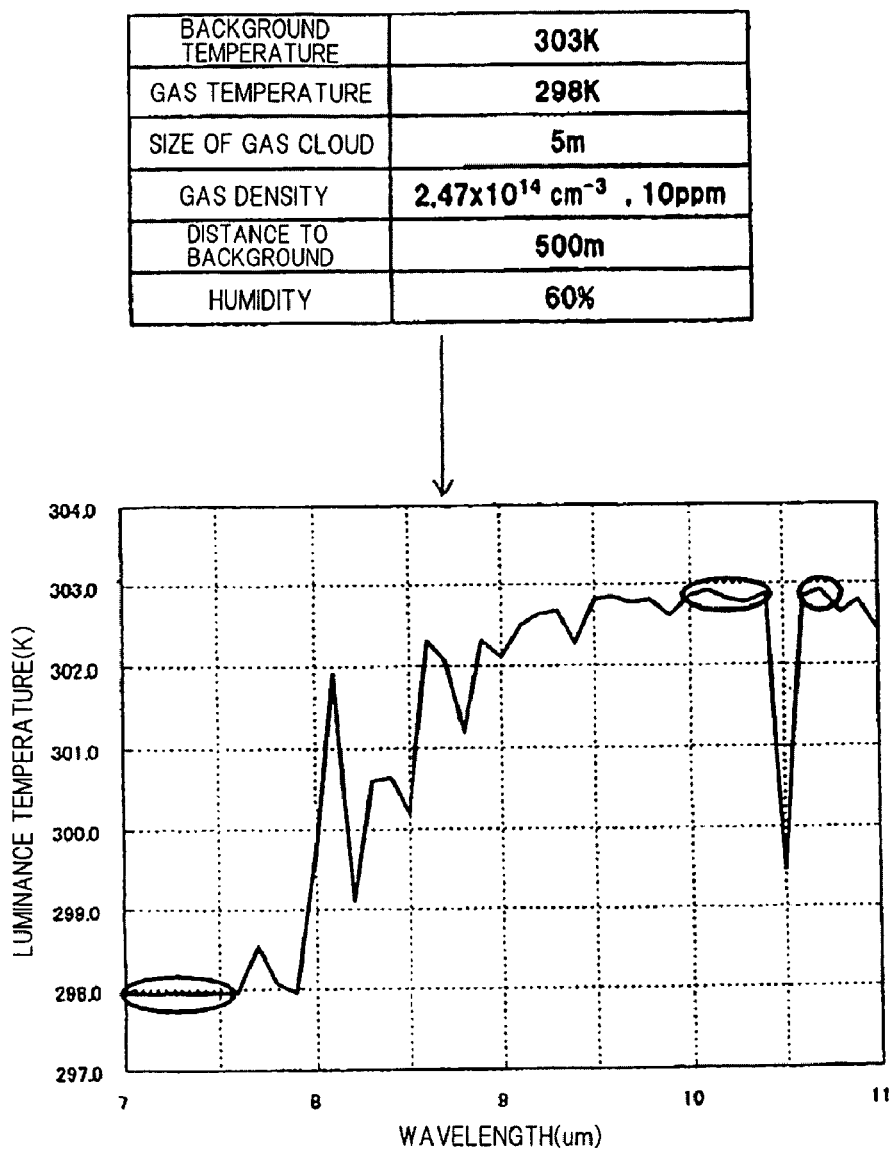
FIG. 9 is an illustration showing radiance temperature spectrum data in the case where the distance to background 5c is changed in FIG. 4.
Figure 10:
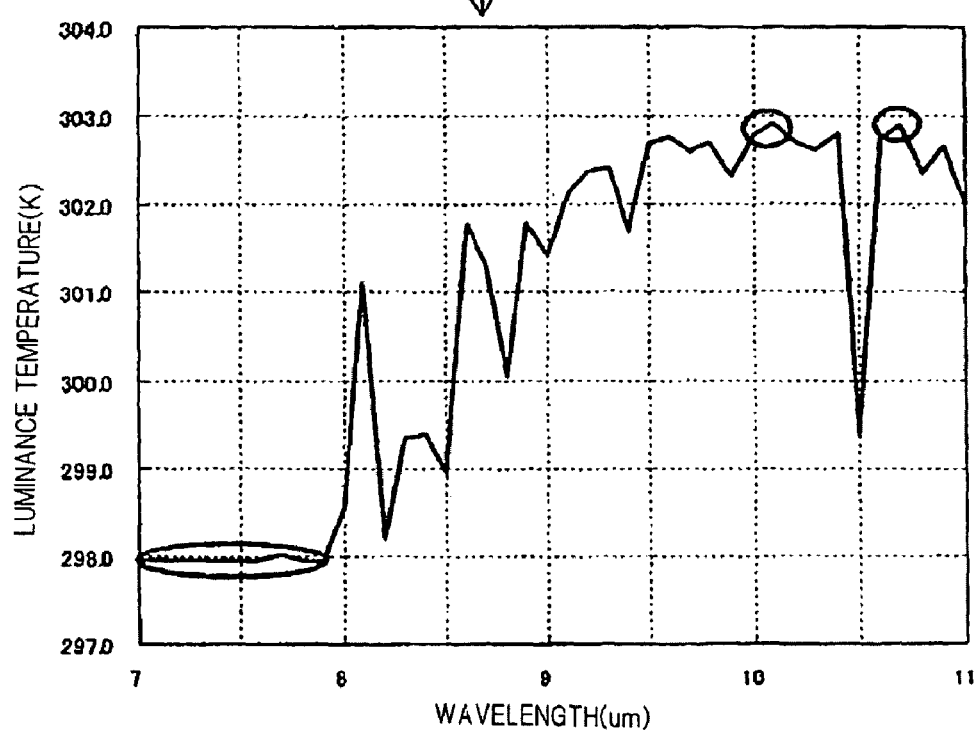
FIG. 10 is an illustration showing radiance temperature spectrum data in the case where the distance to background 5c is changed in FIG. 4.

FIG. 6 is an illustration showing radiance temperature spectrum data obtained by converting the infrared spectrum data shown in FIG. 5.

Then, in step 304, background temperature detecting section 23 detects the maximum radiance temperature from among the radiance temperatures represented by the radiance temperature spectrum data, as temperature (A) of background 5c (see FIG. 6). Background temperature detecting section 23 supplies temperature (A) of background 5c to computing section 25.

Further, in step 305, gas temperature detecting section 24 detects temperature (B) of measuring object gas 5a by using a radiance temperature in a wavelength band included in the water vapor absorption band in the infrared region from among the radiance temperatures represented by the radiance temperature spectrum data.

Among the infrared rays from background 5c of measuring object gas 5a, the light of the water vapor absorption band in the infrared region is absorbed by water vapor. Therefore, in the radiance temperature spectrum data, the radiance temperature in the wavelength band included in the water vapor absorption band is not based on the light from background 5c of measuring object gas 5a, but mostly represents the temperature of water vapor.

Therefore, it is thought that in the radiance temperature spectrum data, the minimum radiance temperature in the wavelength band included in the water vapor absorption band represents the temperature of water vapor. At present, water vapor universally exists in the earth's atmosphere. For this reason, it is thought that the temperature of water vapor represents the temperature of the earth's atmosphere. Measuring object gas 5a also exists in the earth's atmosphere. For this reason, it is thought that the temperature of measuring object gas 5a is equal to the temperature of the earth's atmosphere, that is, the temperature of water vapor.

Gas temperature detecting section 24 uses a wavelength band (for example, 7 to 7.3 micrometers) included in the wavelength band of 5 to 8 micrometers, as the wavelength band included in the water vapor absorption band in the infrared region.

Gas temperature detecting section 24 detects the minimum radiance temperature in the wavelength band included in the water vapor absorption band in the infrared region from among the radiance temperatures represented by the radiance temperature spectrum data, that is, detects the temperature of water vapor as temperature (B) of measuring object gas 5a. Gas temperature detecting section 24 supplies temperature (B) of measuring object gas 5a to computing section 25.

Note that when the distance to background 5c is measured by distance measuring section 4, gas temperature detecting section 24 adjusts, on the basis of the distance to background 5c measured by distance measuring section 4, the wavelength band which is included in the water vapor absorption band in the infrared region and which is used to measure the temperature of measuring object gas 5a.

For example, gas temperature detecting section 24 increases the width of the wavelength band included in the water vapor absorption band in the infrared region as the increase in the measured distance.

Then, in step 306, computing section 25 (specifically calculating section 25b) computes difference ($\Delta T$) between temperature (A) of background 5c and temperature (B) of measuring object gas 5a.

Then, in step 307, calculating section 25b calculates the surface density (nL) of measuring object gas 5a by using the data in storage section 25a, the difference ($\Delta T$), and the variation ($\Delta I$) in intensity of the infrared ray.

For example, calculating section 25b calculates surface density (nL) of measuring object gas 5a by using following Formula 1.

$$nL = \Delta I / (A(\lambda, T_b) \cdot \alpha_\lambda \cdot \Delta T) \qquad \text{Formula 1}$$

In formula 1, $A(\lambda, T_b)$ is a primary differential value of the Planck function, and $\alpha_\lambda$ is an absorption coefficient of measuring object gas 5a. Formula 1, $A(\lambda, T_b)$ and $\alpha_\lambda$ are stored beforehand in storage section 25a.

Formula 1 is derived from the following relations.

It is known that the intensity ($N_{\lambda,r}$) of light taken into gas measuring apparatus 100 is well approximated by Formula 2 (see non-patent document 1, and the like).

$$N_{\lambda,r} = \epsilon_b \cdot B(\lambda, T_b) e^{-\alpha_\lambda nL} + (1 - e^{-\alpha_\lambda nL}) B(\lambda, T_g) \qquad \text{Formula 2}$$

In Formula 2, the term $\epsilon_b \cdot B(\lambda, T_b) e^{-\alpha_\lambda nL}$ represents the intensity of light from background 5c under the situation in which measuring object gas 5a exists.

The term $(1 - e^{-\alpha_\lambda nL}) B(\lambda, T_g)$ represents the intensity of light from measuring object gas 5a under the situation in which background 5c exists. Note that $\epsilon_b$ is the radiation factor of background 5c, $\lambda$ is the wavelength, $T_b$ is the temperature of background 5c, and $T_g$ is the temperature of measuring object gas 5a. The term $B(\lambda, T_b)$ is Planck's formula which represents the radiation of light of wavelength $\lambda$ from the black body at temperature $T_b$. The term $B(\lambda, T_g)$ is Planck's formula which represents the radiation of light of wavelength $\lambda$ from the black body at temperature $T_g$.

Here, in the case where the gas is optically thin, the value of $\alpha_\lambda nL$ is small ($\alpha_\lambda nL \ll 1$). Thus, when in formula 2, an approximation is performed such that $e^{-\alpha_\lambda nL} = (1 - \alpha_\lambda nL)$, Formula 3 is obtained.

$$N_{\lambda,r} \approx \epsilon_b \cdot B(\lambda, T_b)(1 - \alpha_\lambda nL) + \alpha_\lambda nL B(\lambda, T_g) \qquad \text{Formula 3}$$

$$= \epsilon_b \cdot B(\lambda, T_b) + \alpha_\lambda nL(B(\lambda, T_g) - \epsilon_b \cdot B(\lambda, T_b))$$

Here, soil, a plant, and the like, serving as background 5c have $\epsilon_b \approx 1$ in the wavelength band of 8 to 12 micrometers. Thus, when in formula 3, an approximation is performed such that $\epsilon_b = 1$, Formula 4 is obtained.

$$N_{\lambda,r} \approx B(\lambda, T_b) + \alpha_\lambda nL(B(\lambda, T_g) - B(\lambda, T_b)) \qquad \text{Formula 4}$$

Here, when Formula 4 is approximated by using formula $T_g = T_b \Delta T$, Formula 5 is obtained.

$$N_{\lambda,r} \approx B(\lambda, T_b) + \alpha_\lambda nL(dB/dT)\Delta T = B(\lambda, T_b) + A(\lambda, T_b)\alpha_\lambda nL\Delta T \qquad \text{Formula 5}$$

In formula 5, $B(\lambda, T_b)$ represents the radiation from background 5c. For this reason, the term $A(\lambda, T_b) \alpha_\lambda nL\Delta T$ of Formula 5 becomes $\Delta I$.

Thus, Formula 6 is obtained.

$$A(\lambda, T_b)\alpha_\lambda nL\Delta T = \Delta I \qquad \text{Formula 6}$$

Formula 1 is obtained from Formula 6.

Then, display section 3 displays a video image corresponding to the output of two-dimensional infrared detector 12, on the basis of the output of two-dimensional infrared detector 12 supplied from image acquiring section 13b. For example, display section 3 displays an image of measurement area 5 as the video image corresponding to the output of two-dimensional infrared detector 12.

Further, display section 3 displays the surface density of measuring object gas 5a computed by computing section 25, on the video image corresponding to the output of two-dimensional infrared detector 12.

FIG. 7 to FIG. 10 are illustrations showing the radiance temperature spectrum data at the time when the distance to background 5c is changed in the example shown in FIG. 4.

FIG. 11 is an illustration showing a wavelength range that is used to obtain temperature (B) of measuring object gas 5a and temperature (A) of background 5c with a temperature accuracy of 0.2° C. from the radiance temperature spectrum data shown in each of FIG. 6 to FIG. 10.

Note that the wavelength range shown in FIG. 11 is an example, and can be suitably changed according to, for example, the temperature accuracy required of gas measuring apparatus 100.

As shown in FIG. 11, the width of wavelength range, in which temperature (B) of measuring object gas 5a can be detected with high accuracy, is increased as the distance to background 5c is increased.

For this reason, in the exemplary embodiment, as the measured distance increases, gas temperature detecting section 24 increases the width of the wavelength band which is included in the water vapor absorption band in the infrared region and which is used to measure temperature (B) of measuring object gas 5a, that is, the water vapor temperature.

According to the exemplary embodiment, gas temperature detecting section 24 detects the temperature of measuring object gas by using the radiance temperature in the wavelength band included in the water vapor absorption band in the infrared region from among the radiance temperatures represented by the radiance temperature spectrum data.

The water vapor absorption band in the infrared region is in the wavelength band of about 5 to 8 micrometers. For this reason, infrared detecting section 1 does not need to detect the infrared ray up to the wavelength of 14.5 micrometers.

Therefore, according to the exemplary embodiment, it is possible to use, as infrared detecting section 1, not only an infrared detecting section having an infrared sensor whose cutoff wavelength is set close to 14.5 micrometers, but also an infrared detecting section having an infrared sensor whose cutoff wavelength is shorter than 14.5 micrometers.

For this reason, it is possible to use, as infrared detecting section 1, an infrared detecting section having a two-dimensional infrared sensor whose cutoff wavelength is about 11 micrometers, or an infrared detecting section having a single element infrared sensor whose cutoff wavelength is about 11 micrometers.

Therefore, it is possible to ease the restriction on infrared detecting section 1.

Further, in the exemplary embodiment, the resolution of infrared spectrum data is lower than the resolution of the apparatus described in non-patent document 1. For this reason, it is possible to more easily detect the radiance temperature corresponding to the water vapor absorption band in the infrared region.

In the exemplary embodiment, gas temperature detecting section 24 uses a wavelength band included in the wavelength band of 5 to 8 micrometers as the wavelength band included in the water vapor absorption band in the infrared region.

In this case, as described above, it is possible to use, as infrared detecting section 1, not only an infrared detecting section having an infrared sensor whose cutoff wavelength is close to 14.5 micrometers, but also an infrared detecting section having an infrared sensor whose cutoff wavelength is shorter than 14.5 micrometers. Therefore, it is possible to ease the restriction on infrared detecting section 1.

In the exemplary embodiment, infrared detecting section 1 includes interference section 11, two-dimensional infrared detector 12, and arithmetic operation section 13.

Interference section 11 divides the infrared ray received from measurement area 5 into a plurality of infrared rays, and generates interference light by synthesizing the plurality of infrared rays while changing the optical path difference between the plurality of infrared rays. When there is no optical path difference between the plurality of infrared rays, the interference light represents the image of measurement area 5.

Two-dimensional infrared detector 12 receives the interference light from interference section 11. Therefore, when there is no optical path difference between the plurality of infrared rays, the output of two-dimensional infrared detector 12 represents the image of measurement area 5.

Arithmetic operation section 13 outputs infrared spectrum data by using the output of two-dimensional infrared detector 12. Further, display section 3 displays a video image corresponding to the output of two-dimensional infrared detector 12.

For this reason, the output of two-dimensional infrared detector 12 can be used to generate the infrared spectrum data and can be used as the video image of measurement area 5.

Further, two-dimensional infrared detector 12 is used as the infrared detector, and hence it is possible to output the video image data of measurement area 5 in a shorter period of time as compared with the case where a single element infrared detector is used.

In the exemplary embodiment, display section 3 further displays the surface density of measuring object gas 5*a* computed by computing section 25 on the video image corresponding to the output of two-dimensional infrared detector 12.

In this case, it is possible to simultaneously display measurement area 5 and the surface density of measuring object gas 5*a* which exists in measurement area 5. This enables the user to easily understand the region where measuring object gas 5*a* exists.

In the exemplary embodiment, gas temperature detecting section 24 adjusts, on the basis of the distance to background 5*c*, the wavelength band included in the water vapor absorption band in the infrared region.

When the distance to background 5*c* is long, the amount of water vapor contained in measurement area 5 is increased. For this reason, in the water vapor absorption band, the light from background 5*c* is easily absorbed. Therefore, the radiance temperature in the water vapor absorption band is liable to reflect the temperature of water vapor, that is, the temperature of measuring object gas 5*a*.

Therefore, it is possible to improve accuracy in detecting the temperature of measuring object gas 5*a*.

In the exemplary embodiment, gas temperature detecting section 24 increases the wavelength band included in the water vapor absorption band in the infrared region as the distance to background 5*c* increases.

In this case, it is possible to improve the accuracy in detecting the temperature of measuring object gas 5*a*.

Next, a second exemplary embodiment will be described.

Figure 12:
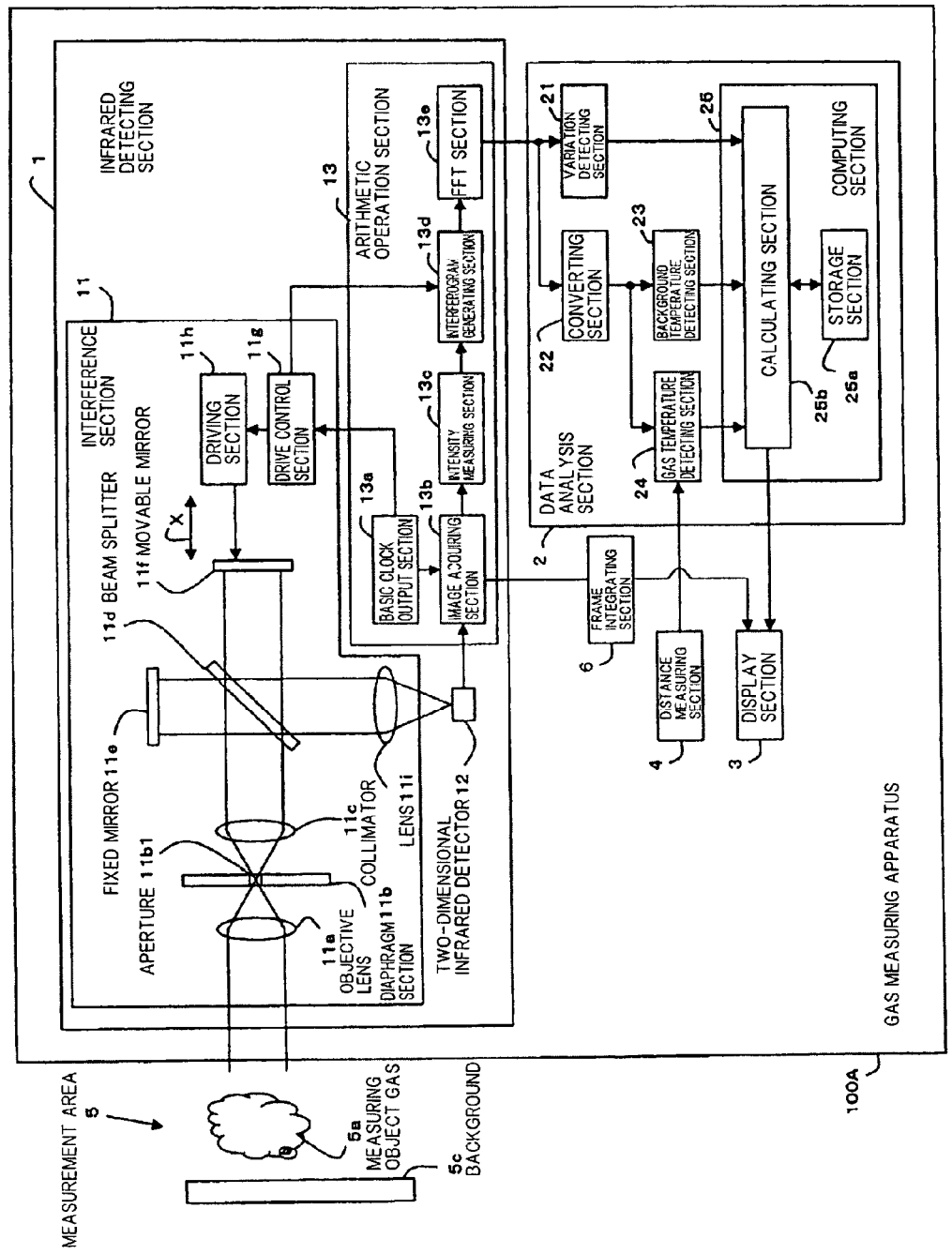
FIG. 12 is a figure showing gas measuring apparatus 100A according to a second exemplary embodiment.

FIG. 12 is a figure showing gas measuring apparatus 100A according to a second exemplary embodiment. In FIG. 12, the same components as those shown in FIG. 1 are denoted by the same reference numerals and characters.

In the following, the second exemplary embodiment will be described focusing on points different from the first exemplary embodiment.

As compared with the first exemplary embodiment (gas measuring apparatus 100), frame integrating section 6 is added in the second exemplary embodiment (gas measuring apparatus 100A).

Frame integrating section 6 can generally be referred to as adjusting means.

Frame integrating section 6 receives, from image acquiring section 13*b*, the output generated each time two-dimensional infrared detector 12 receives interference light that made from lights that are passed through different optical paths, and adds the received outputs. Frame integrating section 6 supplies the added outputs of two-dimensional infrared detector 12 to display section 3.

Display section 3 displays a video image (for example, image of measurement area 5) corresponding to the added outputs of two-dimensional infrared detector 12.

In the exemplary embodiment, frame integrating section 6 receives, from image acquiring section 13*b*, the output generated by two-dimensional infrared detector 12 each time two-dimensional infrared detector 12 receives the interference light that made from lights that are passed through different optical paths, and adds the received outputs.

Generally, when a signal is added N times, the signal to noise ratio is improved by the square root of N times. In the case of the exemplary embodiment, since the signal is different for each optical path, the improvement rate is lower than the square root of N times, but the signal to noise ratio is improved as compared the case where the signal is not added.

Next, a third exemplary embodiment will be described.

Figure 13:
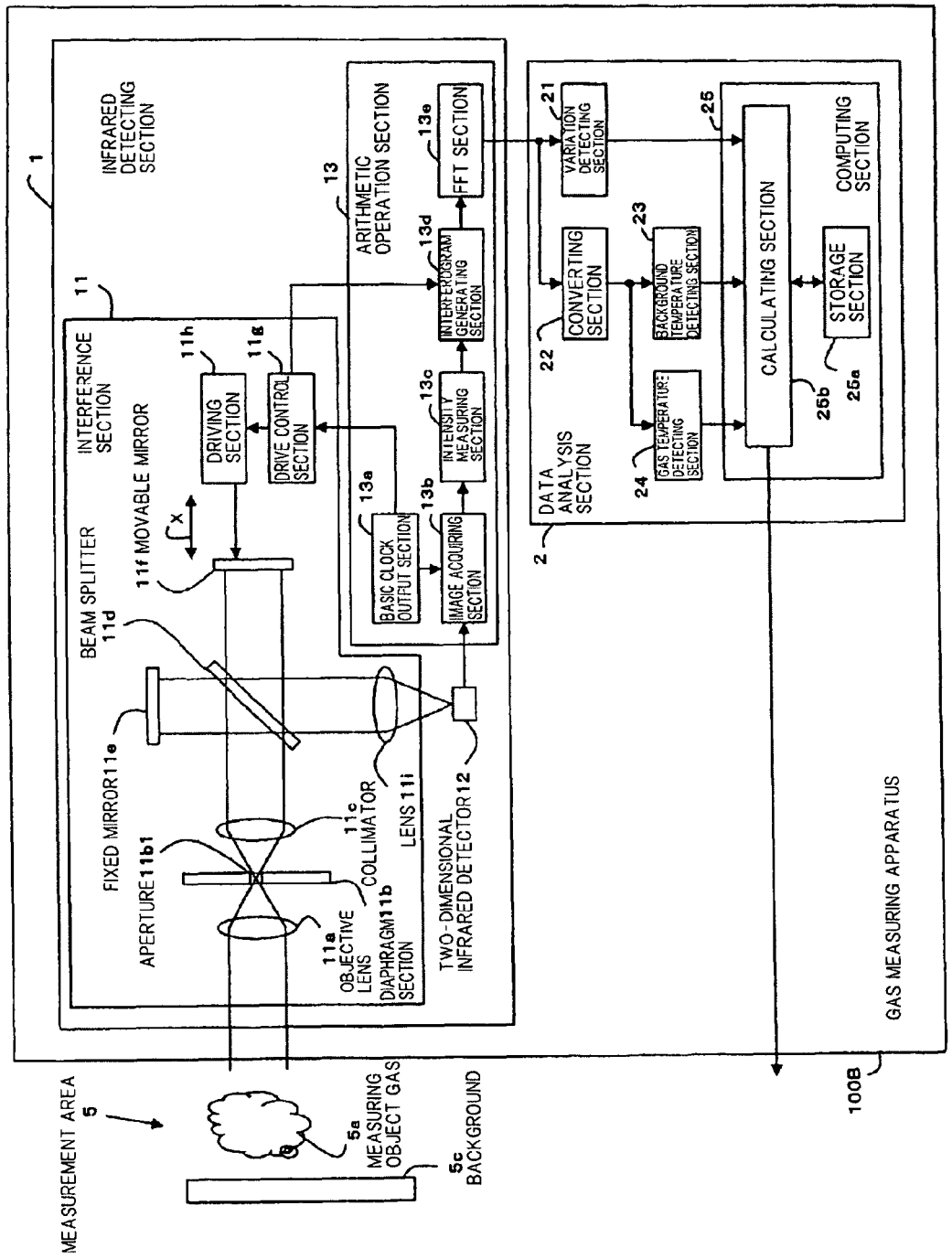
FIG. 13 is a figure showing gas measuring apparatus 100B according to a third exemplary embodiment.

FIG. 13 is a figure showing gas measuring apparatus 100B according to the third exemplary embodiment. In FIG. 13, the same components as those shown in FIG. 1 are denoted by the same reference numerals and characters.

In the following, the third exemplary embodiment will be described focusing on points different from the first exemplary embodiment.

As compared with the first exemplary embodiment (gas measuring apparatus 100), display section 3 and distance measuring section 4 are omitted in the third exemplary embodiment (gas measuring apparatus 100B).

According to the exemplary embodiment, gas measuring apparatus 100B includes infrared detecting section 1, variation detecting section 21, converting section 22, background temperature detecting section 23, gas temperature detecting section 24, and computing section 25, and hence, as described in the first exemplary embodiment, it is possible to ease the restriction on infrared detecting section 1.

In each of exemplary embodiments as described above, the illustrated configuration is a mere example and the present invention is not limited to the illustrated configuration.

For example, when the measuring object gas is observed from different directions by using two gas measuring apparatuses, it is possible to estimate the size (L) of the measuring object gas cloud.

In this case, it is possible to derive the density of the measuring object gas by using the size (L) of the measuring object gas cloud and the surface density of the measuring object gas.

Figure 14:
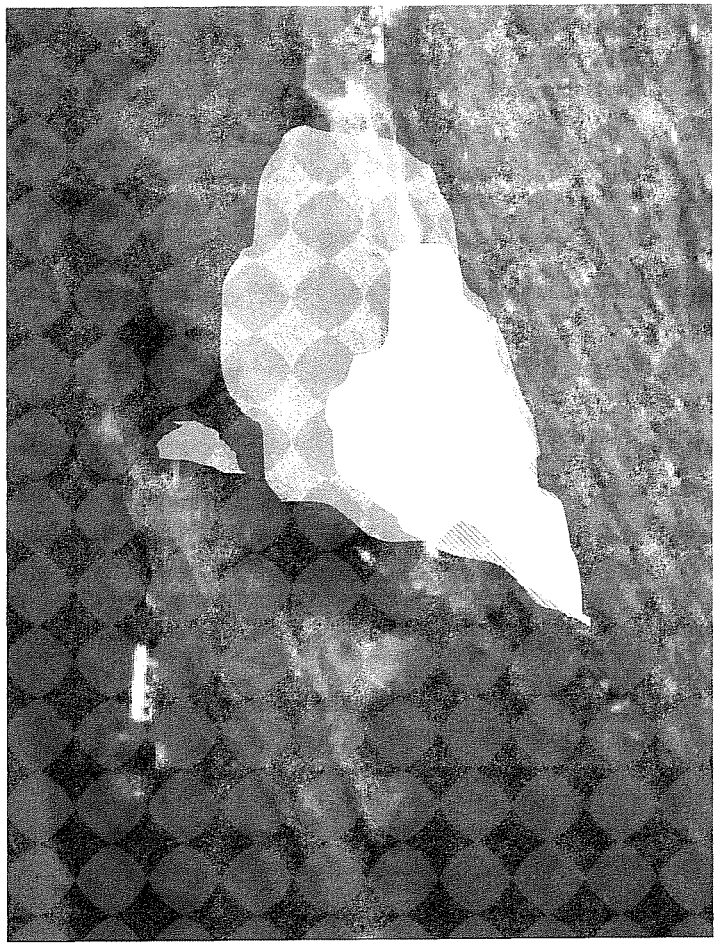
FIG. 14 is an illustration showing a display example of display section 3.

Further, in this case, as shown in FIG. 14, display section 3 may display and superimpose the size (L) of the measuring object gas cloud on the video image corresponding to the output of two-dimensional infrared detector 12.

An exemplary advantage according to the present invention is that it is possible to ease restrictions on the infrared detecting section in the gas measuring apparatus.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

What is claimed is:

1. A gas measuring apparatus comprising:
   an infrared detecting section that receives an infrared ray from a measurement area and outputs infrared spectrum data relating to the infrared ray;
   a variation detecting section that detects, by using the infrared spectrum data, a variation in intensity of the infrared ray, which is caused in the infrared ray that radiates from the measurement area and which is caused by a measuring object gas in the measurement area;
   a converting section that converts the infrared spectrum data to radiance temperature spectrum data which represent wavelengths in an infrared region and radiance temperatures at each wavelength;
   a background temperature detecting section that detects, as background temperature of the measuring object gas, a maximum radiance temperature from among radiance temperatures represented by the radiance temperature spectrum data;
   a gas temperature detecting section that detects the temperature of the measuring object gas by using the radiance temperature in a wavelength band included in the water vapor absorption band in the infrared region from among the radiance temperatures represented by the radiance temperature spectrum data; and
   a computing section that computes surface density of the measuring object gas on the basis of the variation in intensity of the infrared ray, the background temperature of the measuring object gas, and the temperature of the measuring object gas.

2. The gas measuring apparatus according to claim 1, wherein the gas temperature detecting section uses, as the wavelength band included in the water vapor absorption band in the infrared region, a wavelength band included in a wavelength band of 5 to 8 micrometers.

3. The gas measuring apparatus according to claim 1, wherein the infrared detecting section comprises:
   an interference section that divides the infrared ray received from the measurement area into a plurality of infrared rays and generates an interference light beam by synthesizing the plurality of infrared rays while changing optical path differences between the plurality of infrared rays;
   a two-dimensional infrared detecting section that receives the interference light beam; and
   an arithmetic operation section that measures intensity of the interference light beam on the basis of the output of the two-dimensional infrared detecting section, generates an interferogram representing a relationship between the intensity of the interference light beam and the optical path difference, and outputs the infrared spectrum data by Fourier transforming the interferogram,
   further comprises a display section that displays a video image corresponding to the output of the two-dimensional infrared detecting section.

4. The gas measuring apparatus according to claim 3, further comprising an adjusting section that adds an output generated by the two-dimensional infrared detecting section each time the two-dimensional infrared detecting section receives the interference light beam of the different optical path difference,
   wherein the display section displays a video image corresponding to the added output of the two-dimensional infrared detecting section.

5. The gas measuring apparatus according to claim 3, wherein the display section further displays the computed surface density of the measuring object gas on the video image corresponding to the output of the two-dimensional infrared detecting section.

6. The gas measuring apparatus according to claim 1, further comprising a distance measuring section that measures a distance to the background of the measuring object gas,
   wherein the gas temperature detecting section adjusts, on the basis of the measured distance, the wavelength band included in the water vapor absorption band in the infrared region.

7. The gas measuring apparatus according to claim 6, wherein the gas temperature detecting section increases the width of the wavelength band included in the water vapor absorption band in the infrared region as the measured distance increases.

8. A gas measuring method performed by a gas measuring apparatus, comprising:
   outputting, upon receipt of an infrared ray from a measurement area, infrared spectrum data relating to the infrared ray;
   detecting, by using the infrared spectrum data, a variation in intensity of the infrared ray, which is caused in the infrared ray that radiates from the measurement area and which is caused by a measuring object gas in the measurement area;

converting the infrared spectrum data to radiance temperature spectrum data which represent wavelengths in an infrared region and radiance temperatures at each wavelength;

detecting, as background temperature of the measuring object gas, a maximum radiance temperature from among radiance temperatures represented by the radiance temperature spectrum data;

detecting the temperature of the measuring object gas by using a radiance temperature in a wavelength band included in the water vapor absorption band in the infrared region from among the radiance temperatures represented by the radiance temperature spectrum data; and computing surface density of the measuring object gas on the basis of the variation in intensity of the infrared ray, the background temperature of the measuring object gas, and the temperature of the measuring object gas.

9. The gas measuring method according to claim 8, wherein said detecting the temperature of the measuring object gas comprises using a wavelength band included in a wavelength band of 5 to 8 micrometers as the wavelength band included in the water vapor absorption band in the infrared region.

10. The gas measuring method according to claim 8, wherein said outputting the infrared spectrum data comprises:

dividing the infrared ray received from the measurement area into a plurality of infrared rays, and generating an interference light beam by synthesizing the plurality of infrared rays while changing optical path differences between the plurality of infrared rays;

receiving the interference light beam by a two-dimensional infrared detecting section; and measuring intensity of the interference light beam from the output of the two-dimensional infrared detecting section to generate an interferogram representing a relationship between the intensity of the interference light beam and the optical path difference, and outputting the infrared spectrum data by Fourier transforming the interferogram, further comprises displaying a video image corresponding to the output of the two-dimensional infrared detecting section.

11. The gas measuring method according to claim 10, further comprising adding an output generated by the two-dimensional infrared detecting section each time the two-dimensional infrared detecting section receives the interference light beam of the different optical path difference, wherein said displaying comprises displaying a video image corresponding to the added output of the two-dimensional infrared detecting section.

12. The gas measuring method according to claim 10, wherein said displaying comprises displaying the computed surface density of the measuring object gas on the video image corresponding to the output of the two-dimensional infrared detecting section.

13. The gas measuring method according to claim 8, further comprising measuring a distance to the background of the measuring object gas, wherein said detecting the temperature of the measuring object gas comprises adjusting the wavelength band included in the water vapor absorption band in the infrared region on the basis of the measured distance.

14. The gas measuring method according to claim 13, wherein said detecting the temperature of measuring object gas comprises increasing, as the measured distance increases, the width of the wavelength band included in the water vapor absorption band in the infrared region.

15. A gas measuring apparatus comprising:

infrared detecting means for receiving an infrared ray from a measurement area and outputting infrared spectrum data relating to the infrared ray;

variation detecting means for detecting, by using the infrared spectrum data, a variation in intensity of the infrared ray, which is caused in the infrared ray that radiates from the measurement area and which is caused by a measuring object gas in the measurement area;

conversion means for converting the infrared spectrum data to radiance temperature spectrum data which represent wavelengths in an infrared region and radiance temperatures at each wavelength;

background temperature detecting means for detecting, as background temperature of the measuring object gas, a maximum radiance temperature from among radiance temperatures represented by the radiance temperature spectrum data;

gas temperature detecting means for detecting the temperature of the measuring object gas by using a radiance temperature in a wavelength band included in the water vapor absorption band in the infrared region from among the radiance temperatures represented by the radiance temperature spectrum data; and computing means for computing surface density of the measuring object gas on the basis of the variation in intensity of the infrared ray, the background temperature of the measuring object gas, and the temperature of the measuring object gas.

* * * * *